(12) United States Patent
Ling

(10) Patent No.: US 9,987,325 B2
(45) Date of Patent: Jun. 5, 2018

(54) PLANT EXTRACT COMPOSITION FOR REDUCING LOCALIZED FAT AND PROMOTING WEIGHT LOSS AS WELL AS APPLICATION THEREOF

(71) Applicant: CALIWAY BIOPHARMACEUTICALS CO., LTD., New Taipei (TW)

(72) Inventor: Yu-Fang Ling, Taipei (TW)

(73) Assignee: CALIWAY BIOPHARMACEUTICALS CO., LTD., New Taipei (TW)

( * ) Notice: Subject to any disclaimer, the term of this patent is extended or adjusted under 35 U.S.C. 154(b) by 0 days. days.

(21) Appl. No.: 14/914,971

(22) PCT Filed: Aug. 28, 2015

(86) PCT No.: PCT/CN2015/088340
§ 371 (c)(1),
(2) Date: Feb. 26, 2016

(87) PCT Pub. No.: WO2016/029870
PCT Pub. Date: Mar. 3, 2016

(65) Prior Publication Data
US 2017/0157193 A1    Jun. 8, 2017

Related U.S. Application Data

(60) Provisional application No. 62/042,864, filed on Aug. 28, 2014.

(51) Int. Cl.
| | | |
|---|---|---|
| *A61K 36/00* | (2006.01) | |
| *A61K 36/9066* | (2006.01) | |
| *A61K 31/05* | (2006.01) | |
| *A61K 9/00* | (2006.01) | |
| *A61K 31/12* | (2006.01) | |

(52) U.S. Cl.
CPC ........ *A61K 36/9066* (2013.01); *A61K 9/0019* (2013.01); *A61K 31/05* (2013.01); *A61K 31/12* (2013.01)

(58) Field of Classification Search
CPC .................................................... A61K 36/00
See application file for complete search history.

(56) References Cited

U.S. PATENT DOCUMENTS

| | | | |
|---|---|---|---|
| 6,475,530 B1 | 11/2002 | Kuhrts | |
| 7,977,319 B1 | 7/2011 | Levine | |
| 2004/0146539 A1* | 7/2004 | Gupta | A61K 8/0212 424/401 |
| 2012/0177623 A1 | 7/2012 | Naghavi et al. | |
| 2013/0202572 A1 | 8/2013 | Hastings | |
| 2013/0273175 A1 | 10/2013 | Finley | |
| 2014/0141082 A1 | 5/2014 | Gao | |

FOREIGN PATENT DOCUMENTS

| | | |
|---|---|---|
| CN | 101095665 | 1/2008 |
| CN | 101632655 A | 1/2010 |
| CN | 102357226 | 2/2012 |
| EP | 3187189 A1 | 7/2017 |
| JP | 2007131603 | 5/2007 |
| JP | 2011132151 | 7/2011 |
| TW | 201006474 A | 2/2010 |
| TW | 201201794 A | 1/2012 |
| WO | WO2005065667 | 7/2005 |
| WO | WO2006087759 | 8/2006 |
| WO | WO2007041276 A2 | 4/2007 |
| WO | WO2010048114 A1 | 4/2007 |
| WO | WO2007112996 A2 | 10/2007 |
| WO | WO2013100111 | 5/2015 |

OTHER PUBLICATIONS

Cadena et al, Nanoencapsulation of quercetin and resveratrol into elastic liposomes. Biochimica et biophysica acta, (Feb. 2013) vol. 1828, No. 2, pp. 309-316.*
Meydani et al. "Dietary Polyphenols and Obesity", www.mdpi.com/journal/nutrients, ISSN 2017-6643, Jul. 8, 2010, nutrients.
Baba "Prevalence of overweight and obesity among secondary school children (12-14yr) in the city of Mashhad, Iran, Nov. 2010" Jan. 29, 2017, Clinical Biochemistry, vol. 44, No. 13, Suppl.p. S238-S239.
Perez-Torres, I. et al. "Hibiscus Sabdariffa Linnaeus (Malvaceae), Curcumin and Resveratrol as Alternative Medicinal Agents Against Metabolic Syndrome", 2013, Cardiovascular & Hematological Agents in Medicinal Chemistry, 2013, 11, 25-37. Bentham Science Publishers.
Yang et al. "Resveratrol induces apoptosis and inhibits", adipogenesis in 3T3-L1 adipocytes, Phytotherapy Research, Aug. 7, 2008, 1367-1371, Wiley InterScience (www.interscience.wiley.com).
Rhyu et al. "Effects of Curcuma Longa MeOH extract on adipogenesis and lipolysis in 3T3-L1 adipocyles" Symposium of the Korean Society of Food Science and Nutrition, 2009.

* cited by examiner

*Primary Examiner* — Qiuwen Mi
(74) *Attorney, Agent, or Firm* — WPAT, PC

(57) ABSTRACT

Provided is a composition and a pharmaceutical composition for reducing localized fat or promoting weight loss, wherein the composition comprises a plant extract composition comprising resveratrol and turmeric extract and a weight ratio of resveratrol and turmeric extract ranges from 1:30 to 10:1. The composition and the pharmaceutical composition are primarily administered through localized injection to inhibit the growth of fat cells and promote fat cells apoptosis to reduce adipocytes, decrease localized fat deposition, and promote weight loss, without causing inflammation or necrosis on peripheral cells or tissues to avoid severe pain, so as to avoid inflammation, damage, and pain caused by surgical liposuction or non-surgical lipolysis products such as phosphatidylcholine and sodium deoxycholate.

26 Claims, 11 Drawing Sheets

PLANT EXTRACT COMPOSITION FOR REDUCING LOCALIZED FAT AND PROMOTING WEIGHT LOSS AS WELL AS APPLICATION THEREOF

BACKGROUND OF THE INVENTION

1. Field of the Invention

The present invention relates to a composition, and more particularly to the composition for reducing localized fat or promoting weight loss. The present invention also relates to a method of said composition, and more particularly to the method for reducing localized fat or promoting weight loss. The present invention also relates to a pharmaceutical composition, and more particularly to the pharmaceutical composition for reducing localized fat or promoting weight loss. The present invention also relates to a method of using the pharmaceutical composition, and more particularly to a method of using the pharmaceutical composition for reducing localized fat or promoting weight loss.

2. Description of the Prior Arts

With increasing awareness level in beauty as well as self-health, body shape and weight control, weight loss and body fitness are no longer issues cared only by obese individuals. In view of that, weight loss and fitness center and weight management market are booming, driving the development of diet foods, fitness products, weight loss clinical management, medical equipment, fitness equipment, and so on. According to the report "Global Weight Loss and Gain Market 2009-2014" by Markets, the global weight-management market was expected to be US $586.3 billion in 2014 and $650.9 billion in 2015; wherein the main market scale of United States was expected to reach $310 billion, and the market scale of Europe, $238 billion. The rise of consumer health consciousness especially on the chronic diseases caused by obesity made it was noticed globally. Meanwhile, not only obesity population but also numbers of healthy individual were focused on body weight control and body contouring result in prosperity and continuing growth of body contouring market. The statistics of American Society of Plastic Surgeons (ASPS) showed that demand of body contouring was ranked first in the orthopedic field and will be kept annual growing rate at about 12.3% until 2017. "Global Pipeline Analysis, Competitive Landscape and Market Forecasts" published by Research and Markets showed that global market of body contouring equipment reached $900 million in 2010 and would be $2 billion in 2017. The demand of the body contouring market is huge and keeping growing accompanied by variety of liposuction and lipolysis as well as the high risk and unsafe medical treatments.

Conventional liposuction surgery was developed as early as in the 1970s that the subbasal nerves and blood vessels were damaged greatly because of dry liposuction under negative pressure without any infusion buffer and concomitant with high risk of surgery due to substantial blood loss. Tumescent liposuction and superwet liposuction were developed later wherein tumescent liposuction anesthetic and vasoconstrictor were added in infusion solution while in superwet liposuction equal volume of infusion solution was supplied to replace the removed fat mass. In Tumescent liposuction, even though local anesthesia replaces intravenous anesthesia, large amount of anesthetic requires at least 12 hours to turnover and hence the risks were increased. Superwet liposuction has been adopted recently, which is characterized by equal volume exchange of infusion solution and extracted fat to reduce the chance of overload infusion. However, liposuction sites are limited to abdomen, thighs and other areas with large fat accumulation, and the efficacy and safety of liposuction depend entirely on the skilled operator. Liposuction is a harmful and time-consuming process to body which causes severe postoperative bruising, swelling, pain and sensory paralysis, scar tissue, unsmooth skin surface, and other side effects. In addition, operation time of liposuction is longer as well as increased the blood loss, surgery risk, and the four to six weeks recovery period. Although auxiliary liposuction instrument such as ultrasound and laser are developed, the key factor is still the doctor's skill. Furthermore, tissue burn and poor efficacy are common while using auxiliary liposuction equipment. In view of the drawback in liposuction, the aesthetic medical industry of United States and Europe are focusing on the development of medical equipment since the 1980s. The trend of medical cosmetic equipment for liposuction is minimally invasive and even non-invasive lipolysis. The objects of lipolytic product or equipment are reduced blood loss, shortened recovery period, less invasion, high safety, convenience, and smaller wound accompanied by the advantages of better efficacy and competitive price for aesthetic medical market.

Mesotherapy is a lipolytic method using phosphatidylcholine or sodium deoxycholate as active ingredient to lyse the injected adipose tissues. The structure of phosphatidylcholine and sodium deoxycholate is similar to the component of cell membrane molecules therefore break down the cell membrane of adipocytes and trigger cell necrosis. However, the effect of phosphatidylcholine and sodium deoxycholate is not only specific to adipocytes but also to other surrounding cells which causes a series of inflammation reaction around the injection site with severe pain and swelling and even local tissue necrosis or infection. Although lipolysis injection overcomes the site limitation of using liposuction, one lipolysis injection treatment course may require dozens of injections every 2 weeks for 3 to 6 cycles to reach the goal of body contouring. Even the addition of anesthetic in the lipolysis injection, the injected site may still suffer from severe inflammation and pain after anesthesia withdrawn, longer treatment period and injection dosages are also concerned. Consider of the risks of severe postoperative pain, nerve paralysis, local tissue necrosis or infections, the allowed single injection volume is very limited, only restricted on the application of submental fat, and other potential side effects, most aesthetic medical surgeons are unwilling to use the formulation described for localized fat reduction even that is the first lipolytic formulation approved for sale in the United States.

Overall, more effective, limited side effects, safer, and more application sites products for reducing localized adipose are eager to be launched to fit the demand of the surgeons and consumers as well as the trend of aesthetic medical marker.

SUMMARY OF THE INVENTION

A plant extract composition in accordance with the present invention comprises resveratrol and turmeric extract and a weight ratio of resveratrol and turmeric extract ranges from 1:30 to 10:1. The composition of the present invention not only can inhibit adipocytes growth, but also can induce adipocyte apoptosis to reduce localized fat deposits and adipocytes numbers; the composition reduces the body weight, but does not cause inflammation of the surrounding cells or tissue necrosis. The composition of the present invention would not cause inflammation or severe pain, thus avoid damage and inflammation and pain from liposuction or low-invasive instrument. The composition would not causes necrosis and results in surrounding tissue inflammation and infection as triggered by phosphatidylcholine or sodium deoxycholate.

According to the present invention, the term "turmeric extract" as used herein mainly comprises curcumin Preferably, the amount of the curcumin based on the total amount of the turmeric extract is from 80% to 100%.

In another preferred embodiment, the present invention also provides a pharmaceutical composition for reducing localized fat or promoting weight loss, wherein the pharmaceutical composition comprises a therapeutically effective amount of the plant extract composition as above mentioned mixed with at least a pharmaceutically acceptable excipient, wherein the at least one excipient includes, but is not limited to, salts, stabilizers, bacteriostatic agents, emulsifiers, surfactants, or anesthetics to obtain an injection formulation.

Preferably, the stabilizer includes, but is not limited to, xylitol, sorbitol, polydextrose, isomalt or dextrose.

Preferably, said "at least a pharmaceutically acceptable excipient" includes, but is not limited to, lubricant, suspending agent, solubilizer, glidant, emulsifier or surfactant. The amount of excipient employed will depend upon quantity of the active agent. One excipient can perform more than one function.

Preferably, examples of lubricant includes but are not limited to, agar, ethyl oleate, ethyl laureate, glycerin, glyceryl palmitostearate, hydrogenated vegetable oil, magnesium oxide, magnesium stearate, mannitol, poloxamer, ethylene glycol, sodium benzoate, sodium lauryl sulfate, sodium stearoyl acid, sorbitol, stearic acid, talc, or zinc stearate.

Preferably, examples of suspending agent include, but are not limited to, carboxymethyl cellulose (CMC), CMC-Na, mannitol.

Preferably, examples of solubilizer include, but are not limited to, hydroxypropyl-beta-cyclodextrin, tween 80, or castor oil.

Preferably, examples of glidant include, but are not limited to, magnesium stearate, silicon dioxide, magnesium trisilicate, powdered cellulose, starch, talc, tribasic calcium phosphate, calcium silicate, magnesium silicate, silicon hydrogel.

Preferably, examples of emulsifier might be a naturally occurring phosphatide, including, but not limited to, soybean lecithin, lecithin, monoglycerides, diglycerides, sodium stearate, sorbitan fatty acid esters, or polyoxyethylene sorbitan monooleate.

Preferably, examples of surfactant include, but are not limited to, Tween, polyethylene-polypropylene glycol, polyoxyethylene-monostearate, polyoxyethylene alkyl ethers (e.g. polyoxyethylene lauryl ether alone), Triton-X, polyoxyethylene-polyoxypropylene copolymer, or sodium dodecyl sulfate (SDS).

In accordance with the present invention, the pharmaceutical composition for reducing localized fat or promoting weight loss is prepared for multiple forms, including, but not limited to, liquid, semi-solid and solid dosage, such as liquid solution (including injectable and infusible solution), dispersions, suspensions, powders, lyophilized powders, or liposomes or transdermal ointment or patch. Preferred form depends on the mode of administration and therapeutic application of expectations. Preferably, the pharmaceutical composition of the present invention is administered in the form of infusion solutions, and the preferred mode of administration is infusible solution modes, and the preferred formulation is parenteral, such as injectable solution. In an embodiment of the present invention, the pharmaceutical composition comprises an effective amount of resveratrol and turmeric extract is subcutaneously administered. Preferably, the pharmaceutical composition of the present invention is administered by subcutaneous injection to subcutaneous fat. In another embodiment of the present invention, the formulation of ointment is well known in the art, including, but not limited to, active agent, wax, water, petrolatum, preservatives, higher alcohols, polyhydric alcohols, emulsifiers, solvents, thickeners, plasticizers, fragrances, buffers, antibiotics, stabilizers or mixtures thereof.

The dosage of the pharmaceutical composition of the present invention might be adjusted appropriately according to different parameters. The parameters include, but are not limited to the type of subject, the weight of subject, and the thickness and area of localized fat of subject. The pharmaceutical composition of the present invention can be administered once, repeatedly or continuously administered within 24 hours; also weekly or monthly multiple or continuous administration. Preferably, the injection includes, but is not limited to subcutaneous injection, subcutaneous implantation, intravenous drip, intravenous pumps injection, implantable injection pump.

The present invention further provides a method for reducing localized fat or promoting weight loss comprising a step of administering at a local site of to a subject in need thereof a therapeutically effective amount of the pharmaceutical composition comprising resveratrol and turmeric extract and a pharmaceutically acceptable carrier to make the local site of the subject achieve the effect of inhibit localized adipocyte growth, promote adipocytes apoptosis, decrease fat deposition, and reduce body weight.

Preferably, the subjects are human or animals.

Preferably, the therapeutically effective amount of the pharmaceutical composition is from 0.4 mg/kg BW (Body Weight) to 100 mg/kg BW.

More preferably, the therapeutically effective amount of the pharmaceutical composition is from 1 mg/kg BW to 60 mg/kg BW.

Preferably, the term "reduce body weight" as used herein refers to reduction of body weight gain by 5% to 30%.

According to the present invention, the term "reducing localized fat" as used herein refers to administering an effective amount of pharmaceutical compositions comprising resveratrol and turmeric extract to inhibit the growth of adipocytes, induce adipocytes apoptosis, and reduce localized fat deposition. As shown in the embodiment of the present invention, reducing localized fat can be determined by administering the composition comprising resveratrol and turmeric extract in a specific dosage, and measuring the growth rate of adipocyte, apoptosis level, and subcutaneous fat and visceral fat in a specific period. Preferably, the localized fat includes, but is not limited to, subcutaneous fat, visceral fat, localized deposits fat or adipocytes.

Preferably, the sites of localized fat include, but are not limited to, face, jaw, arm, waist, abdomen or thighs.

The composition or pharmaceutical composition of the present invention is not only significantly superior to that of resveratrol or turmeric extracts administered alone, but also never been a drug for reducing localized fat by localized injection whatever using resveratrol alone or in combination with turmeric extract. Furthermore, the present invention is primarily administered through localized injection to inhibit adipocyte growth and promote adipocyte apoptosis to reduce localized fat, without affecting surrounding cells or tissues and no significant side effect was found in animal study.

Therefore, the combination or pharmaceutical composition of the present invention is safer with fewer side effects. The technical feature of the present invention is totally different from other current techniques or products. Thus, the present invention could be used to avoid local necrosis, severe pain, inflammation and necrosis caused by plastic surgery instruments such as conventional liposuction and ultrasound, or lipolytic ingredients such as phosphatidylcholine and sodium deoxycholate. Moreover, the present invention can also significantly reduce postoperative bruising, swelling, pain and sensory paralysis, as well as shorten recovery period.

DETAILED DESCRIPTION OF THE PREFERRED EMBODIMENTS

Other objectives, advantages and novel features of the invention will become more apparent from the following detailed description when taken in conjunction with the accompanying drawings.

Example 1 Preadipocytes Inhibition Assay

3T3-L1 preadipocytes (purchased from FIRDI, Taiwan) were seeded in 96-well plates to reach $1 \times 10^4$ cells per well. Three repeated cell experiments were examined in seven groups including 1% DMSO as control group, 50 ppm resveratrol, 50 ppm turmeric extract, 80 ppm green tea extract, and the formulations UL003A, UL003C, and UL003R. After incubation for 48 hours, the inhibitory effect on 3T3-L1 preadipocytes was analyzed by MTT assay. The formulation UL003A in accordance with the present invention has a weight ratio 9:1 of resveratrol to green tea extract; the formulation UL003C in accordance with the present invention has a weight ratio 1:19 of resveratrol to turmeric extract; the formulation UL003R in accordance with the present invention has a weight ratio 9:1 of resveratrol to turmeric extract. All data are presented as Mean±SD. The letters a, b, c, d, and e represent the results of the statistics, and the different letters represent statistical difference among the groups ($p<0.05$).

Figure 1:
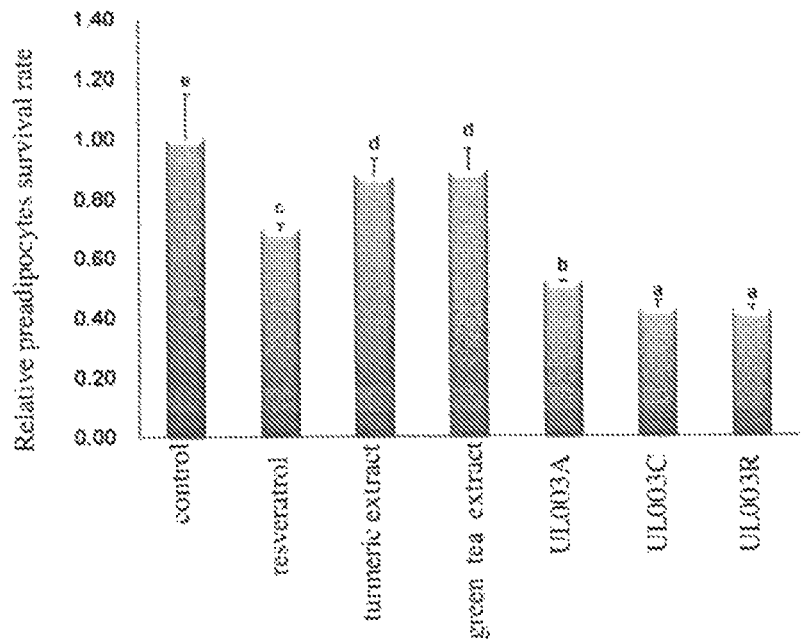
FIG. 1 illustrates the bar chart in each group for inhibiting preadipocytes growth through MTT assay.

As shown in FIG. 1, compared to that of control group, the formulations UL003A, UL003C, and UL003R of the present invention inhibit preadipocytes growth ($p<0.05$). The inhibitory effect of the present invention were significantly better ($p<0.05$) than those of resveratrol, turmeric extract, or green tea extract.

Example 2 Differentiating Adipocytes Inhibition Assay

3T3-L1 preadipocytes cells were seeded in 12-well plates to reach $1 \times 10^5$ cells per well. After the seeding for about four days, medium was replaced and contained 5 μg/ml insulin (differentiation agent), 1 μM dexamethasone, 0.5 mM 3-isobutyl-1-methylxanthine and respective treatment including 1% DMSO, 50 ppm resveratrol, 50 ppm turmeric extract, 80 ppm green tea extract, and 100 ppm formulation UL003A, UL003C, or UL003R in which DMSO was control group. After incubation for another 48 hours, the inhibitory effect on differentiating adipocytes 3T3-L1 was analyzed by MTT assay. All data are presented as Mean±SD and different letters differ significantly among groups ($p<0.05$).

Figure 2:
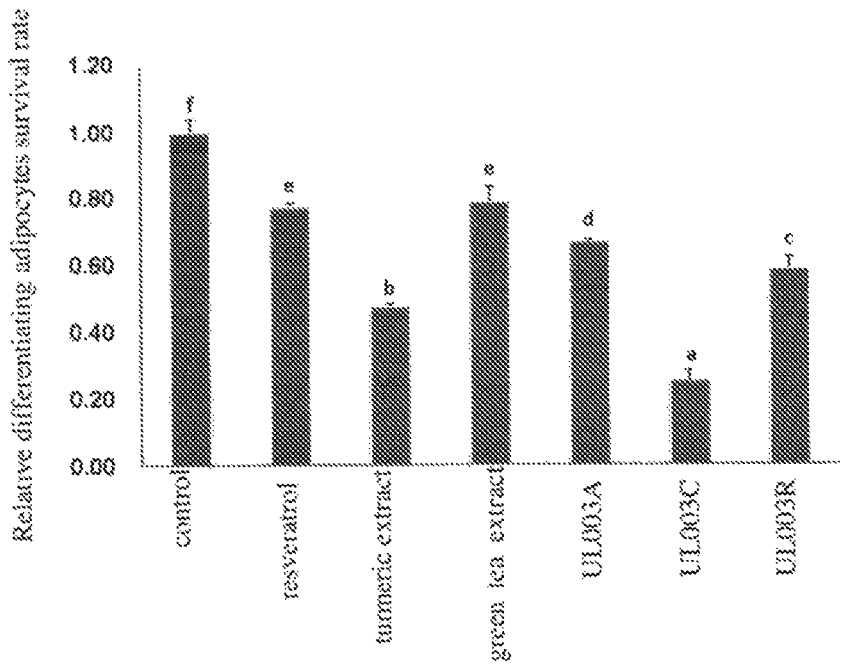
FIG. 2 illustrates the bar chart in each group for inhibiting differentiating adipocytes growth through MTT assay.

As shown in FIG. 2, compared to that of the control group, the formulations UL003A, UL003C, and UL003R of the present invention all could inhibit differentiating adipocytes growth ($p<0.05$), wherein the formulation UL003C had the best inhibitory effect on differentiating adipocytes. The inhibitory effect on differentiating adipocytes by the formulation UL0003C of the present invention was greater than those of resveratrol, turmeric extract or green tea extract ($p<0.05$).

Example 3 Mature Adipocytes Inhibition Assay

The object of the instant example is comparing the inhibitory effect on mature adipocytes of the composition of the present invention and the conventional sodium deoxycholate. 3T3-L1 cells were seeded in 12-well plates to reach $3 \times 10^4$ cells per well. After seeding for about four days, medium was changed and contained 5 μg/ml insulin, 1 μM dexamethasone, and 0.5 mM 3-isobutyl-1-methylxanthine After incubation for another two days, medium was renewed and contained 5 μg/ml insulin for additional four days maturity incubation. Medium containing PBS (as control group), DMSO (as control group), 50 ppm or 100 ppm formulation UL003C and 50 ppm or 100 ppm sodium deoxycholate were respectively added to the 12-well plates for six groups. After incubation for 48 hours, the inhibitory effect on mature adipocytes was analyzed by MTT assay.

Figure 3:
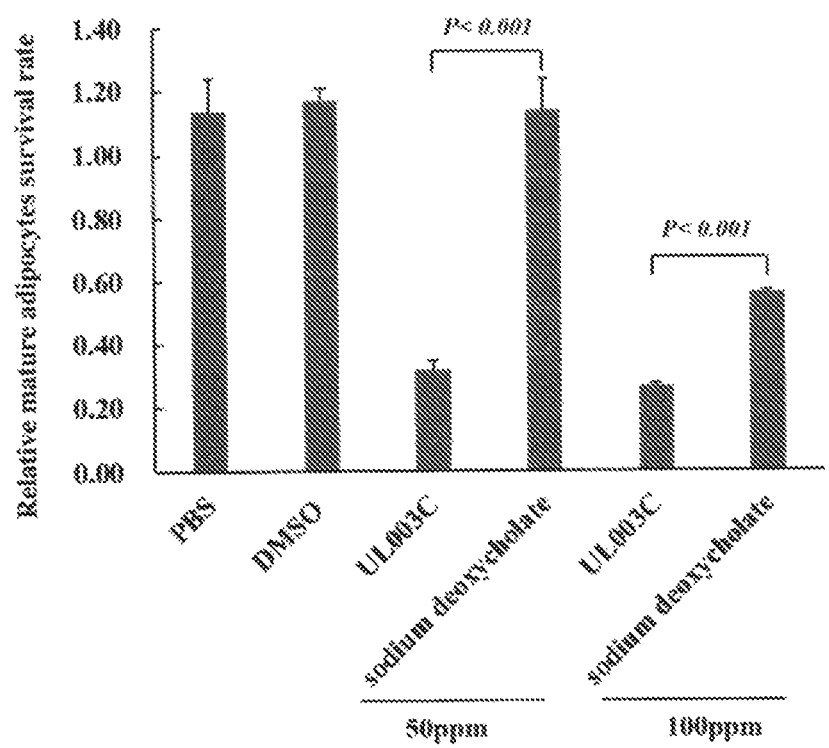
FIG. 3 illustrates the bar chart of the formulation UL003C and sodium deoxycholate for inhibiting mature adipocytes growth through MTT assay.

As shown in FIG. 3, the formulation UL003C of the present invention inhibited mature adipocytes growth (p<0.05) at concentration of 50 ppm or 100 ppm. The inhibitory effect on mature adipocytes of the present invention formulation UL0003C was greater than that of sodium deoxycholate (p<0.001).

Example 4 Apoptosis Assay (I)

3T3-L1 cells were seeded in 12-well plates to reach $1\times10^5$ cells per well. After the seeding for about four days, medium was changed and contained 5 μg/ml insulin, 1 μM dexamethasone, and 0.5 mM 3-isobutyl-1-methylxanthine After incubation for four days for adipocyte differentiation, medium was renewed and contained 5 μg/ml insulin for additional four days incubation. Media containing DMSO and 50 ppm formulations UL003A, UL003C, and UL003R of the present invention were respectively added to the 12-well plates for four groups. Three repeated cell experiments were examined. After incubation for 24 hours, cells were collected and then immunostained by Annexin V/PI antibodies. The level of apoptosis was analyzed with flow cytometer, wherein Annexin $V^-PI^-$ cells represented the survival number of mature adipocytes, and Annexin $V^+PI^+$ cells represented the apoptotic number of mature adipocytes.

Figure 4:
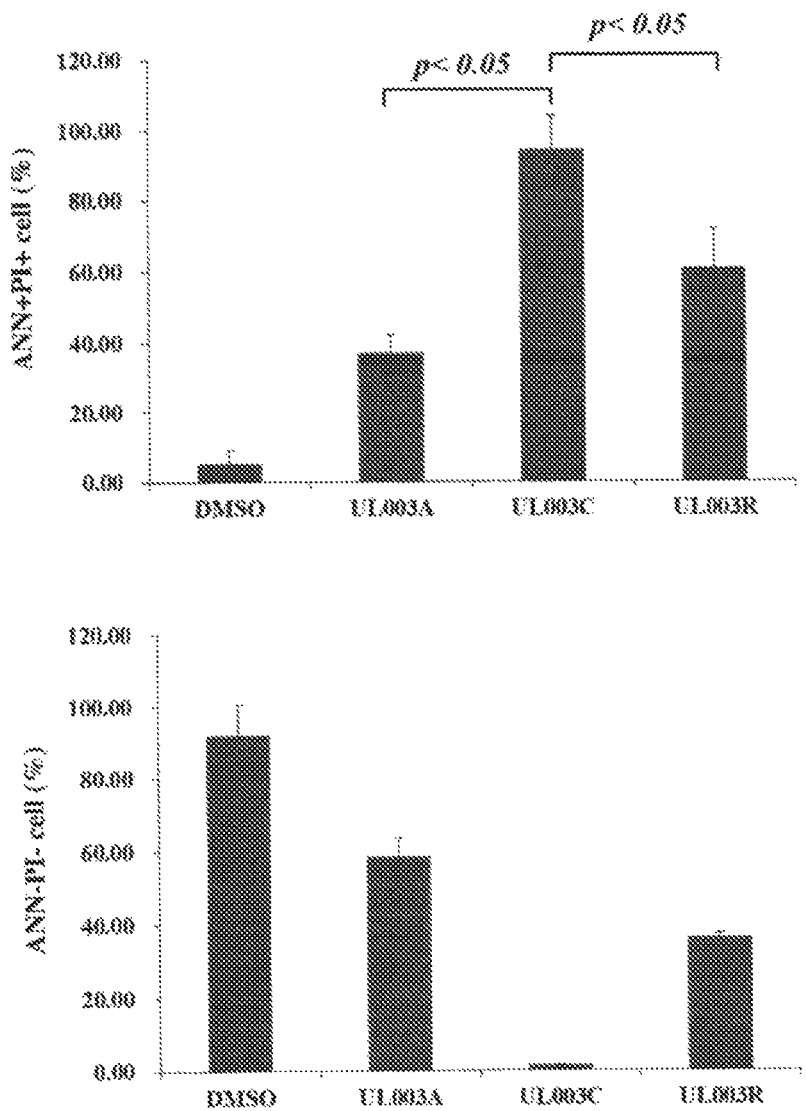
FIG. 4 illustrates the bar chart of the formulations UL003A, UL003C and UL003R for promoting apoptosis after Annexin V/PI staining through flow cytometer.

As shown in FIG. 4, compared to that of control group, the formulations UL003A, UL003C, and UL003R of the present invention all induced mature adipocytes apoptosis (p<0.05), wherein the best apoptotic effect on mature adipocytes was induced by formulation UL003C (p<0.05).

Example 5 Apoptosis Assay (II)

3T3-L1 cells were seeded in 12-well plates to reach $1\times10^5$ cells per well. After seeding for about four days, medium was changed and contained 5 μg/ml insulin, 1 μM dexamethasone, and 0.5 mM 3-isobutyl-1-methylxanthine After incubation for four days for adipocyte differentiation, medium was renewed and contained 5 μg/ml insulin for additional four days maturity incubation. Media containing DMSO (as control group), 50 ppm or 100 ppm formulations UL003A, UL003C, and UL003R of the present invention were respectively added to the 12-well plates for seven groups. Three repeated cell experiments were examined. After incubation for 24 hours, cells were collected and then immunostained by caspase 3 antibody. The level of apoptosis was analyzed by flow cytometry, wherein mature adipocytes having caspase 3 staining underwent apoptosis.

Figure 5:
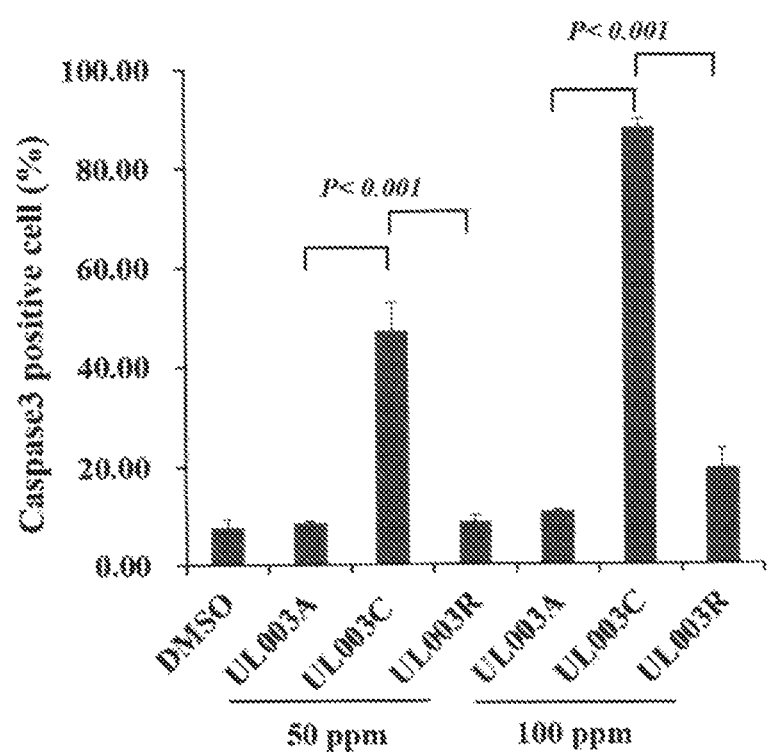
FIG. 5 illustrates the bar chart of the formulations UL003A, UL003C and UL003R for promoting apoptosis after caspase 3 staining through flow cytometer.

As shown in FIG. 5, compared to that of control group, mature adipocytes were treated with 50 ppm or 100 ppm formulation UL003C of the present invention and more caspase 3 stained cells was shown (p<0.001) indicated that formulation UL003C of the present invention induced mature adipocytes apoptosis significantly.

Example 6 Apoptosis Assay (III)

3T3-L1 cells were seeded in 12-well plates to reach $1\times10^5$ cells per well. After the seeding for about four days, medium was changed and contained 5 μg/ml insulin, 1 μM dexamethasone, and 0.5 mM 3-isobutyl-1-methylxanthine After incubation for four days for adipocyte differentiation, medium was renewed and contained 5 μg/ml insulin for additional four days maturity incubation. Medium containing DMSO (as control group), 50 ppm turmeric extract, 50 ppm resveratrol, and 50 ppm or 100 ppm formulation UL003C of the present invention for five groups were respectively added to the 12-well plates. Three repeated cell experiments were examined. Accordingly cells treated by resveratrol for 16 more hours were more likely to express caspase 3 protein, the remaining groups were all incubated for 3 hours, and collected for apoptotic assay with flow cytometry.

Figure 6:
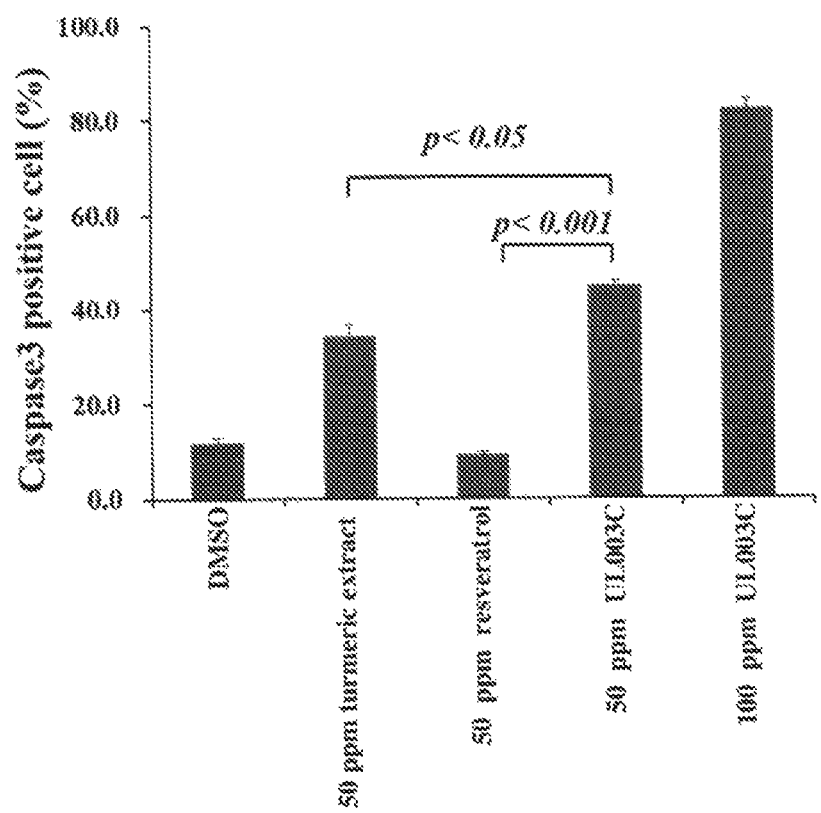
FIG. 6 illustrates the bar chart of resveratrol, turmeric extract and the formulation UL003C for promoting apoptosis after caspase 3 staining through flow cytometer.

As shown in FIG. 6, compared to that of control group, mature adipocytes treated with 50 ppm formulation UL003C of the present invention expressed more caspase 3 protein (p<0.001) indicated that formulation UL003C of the present invention induced mature adipocytes apoptosis. The number of caspase 3 positive mature adipocytes treated by the formulation UL0003C of the present invention was greater than those of the turmeric extract (p<0.05) and the resveratrol (p<0.001) and showed that formulation UL003C of the present invention induced the most mature adipocytes apoptosis than other group.

Example 7 Apoptosis Assay (IV)

The object of the instant example is to compare the apoptosis level on mature adipocytes caused by the composition of the present invention and the well-known sodium deoxycholate. 3T3-L1 cells were seeded in 12-well plates to reach $1\times10^5$ cells per well. After seeding for about four days, medium was changed and contained 5 μg/ml insulin, 1 μM dexamethasone, and 0.5 mM 3-isobutyl-1-methylxanthine After incubation for four days for adipocyte differentiation, medium was renewed and contained 5 μg/ml insulin for additional four days maturity incubation. Medium containing DMSO (as control group), 100 ppm formulation UL003C and 100 ppm sodium deoxycholate were respectively added to the 12-well plates for three groups. Three repeated cell experiments were examined. After incubation for 24 hours, cells were collected and then immunostained by Annexin V/PI antibodies. The level of apoptosis was analyzed by flow cytometry, wherein Annexin $V^-PI^-$ cells represented the survival number of mature adipocytes, and Annexin $V^+PI^+$ cells represented the apoptotic number of mature adipocytes.

Figure 7:
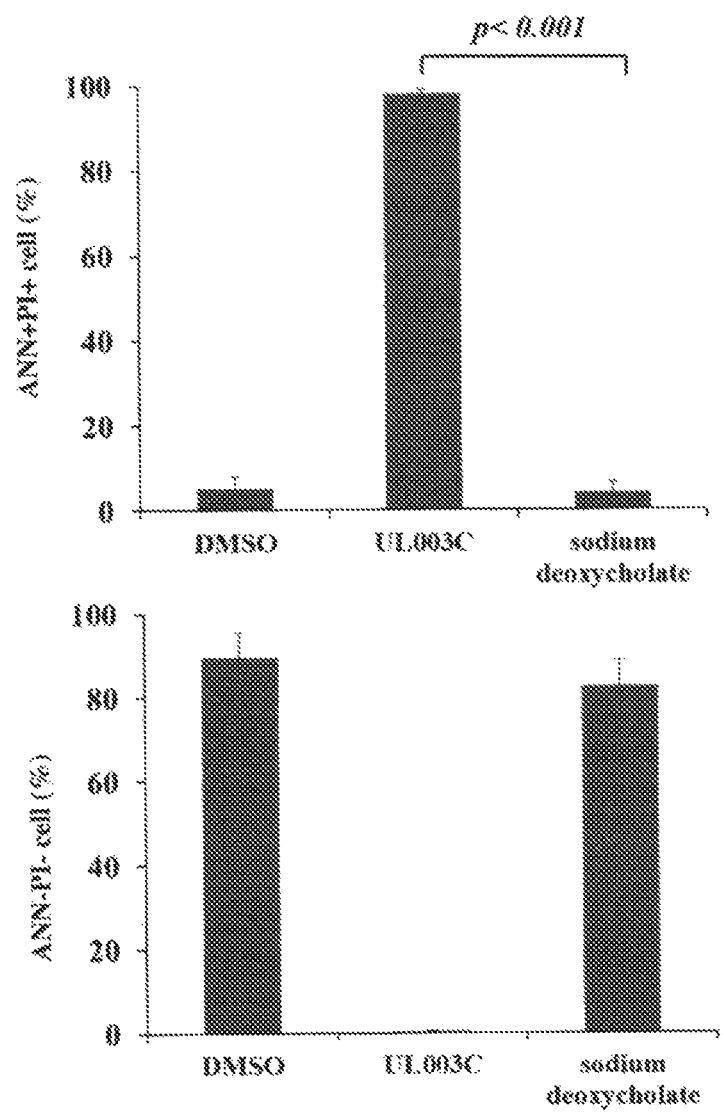
FIG. 7 illustrates the bar chart of the formulation UL003C and sodium deoxycholate for promoting apoptosis after Annexin V/PI staining through flow cytometer.

As shown in FIG. 7, compared to that of control group and sodium deoxycholate, the formulation UL003C of the present invention could significantly induce mature adipocytes apoptosis (p<0.001). On the contrary, compared to that of control group, no statistical significance (p>0.05) was found in sodium deoxycholate group indicated that only formulation UL003C of the present invention induced mature adipocytes apoptosis.

Example 8 Animal Assay (I)

Sprague-Dawley (SD) male rats aged 8 weeks were used in this example. Three groups including control group, low-dose experimental group (formulation UL003C-20: 20 mg/kg BW), and high-dose experimental group (formulation UL003C-40: 40 mg/kg BW) were examined and four male rats were used in each group from 207 g±6 g body weight. After high fat diets treatment to reach to 330 g±10 g body weight, low-dose or high-dose composition of the present invention were injected into bilateral subcutaneous lower groin adipose tissue in two sites (5 mg/kg/site), and the dosages for rats in low-dose experimental group and high-dose experiment group were 20 mg/kg/time and 40 mg/kg/time respectively; the dosage for control group was 4 ml/kg/time sterile water for one injection. The formulation UL003C of the present invention and sterile water were administrated at the first, third day, and fifth day. Body-weight and diet intake were recorded daily. In the end of the experiment (the 21th day), the rats were weighed and then fasted for 12-14 hours. The serum biochemical markers of glutamic pyruvic transaminase (GPT), glutamate oxalacetate aminotransferase (GOT), creatinine and urea were measured from blood sampling to evaluate the hepatic and renal function. After rats were sacrificed humanely, subcutaneous abdominal fat, upper groin fat, and lower groin fat were removed and weighed. All data are presented as Mean±SD and different letters differ significantly among groups ($p<0.05$).

Figure 8:
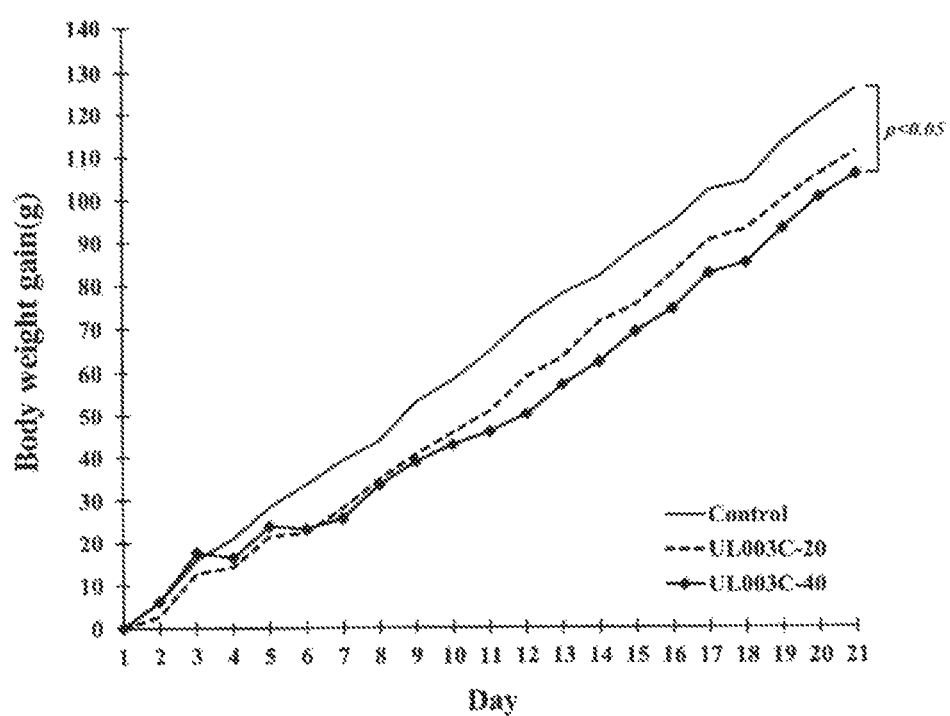
FIG. 8 shows the curves of weight gain in each group related to rats administered with high-fat diet (Control) to induce localized fat increasing and then localized injection.

As shown in FIG. 8, the weight gains of the low-dose group and high-dose group were lower than that of control group, wherein the weight gain of rats administered with the formulation UL003C-40 was significantly lower than that of control group ($p<0.05$) and reach 15.8%. The loss of weight gain of formulation UL003C-20 group was decreased 11.1% without statistical difference compared to that of control group ($p>0.05$). The results showed that the composition of the present invention can reduce the body weight, in a dose-response manner.

Figure 9:
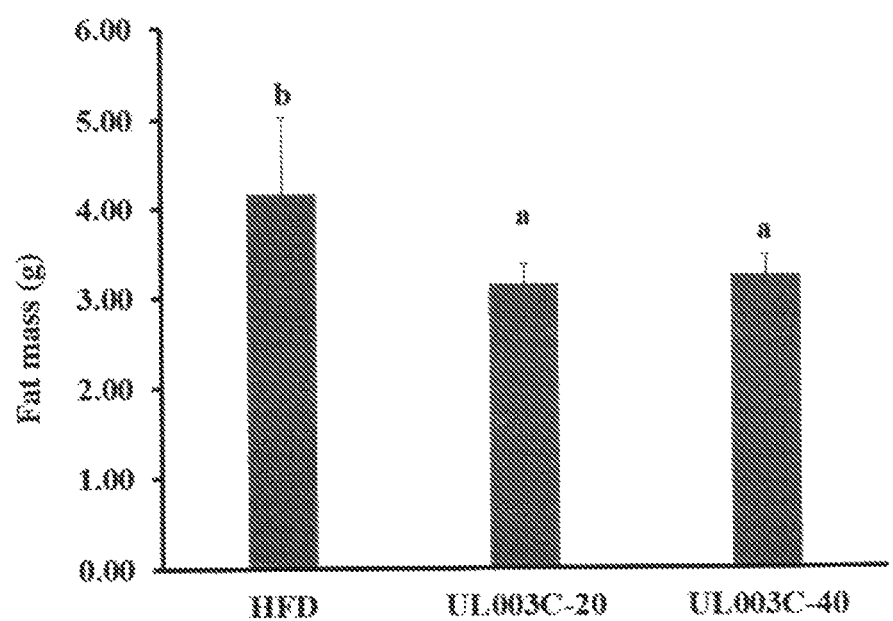
FIG. 9 shows the subcutaneous fat mass in each group related to rats administered with high-fat diet (Control) to induce localized fat increasing and then localized injection.

As shown in FIG. 9, compared to that of control group, the formulation UL003C of the present invention significantly reduced injected subcutaneous fat ($p<0.05$) and reach 24.3% ($p<0.05$) in formulation UL003C-20 group and 21.6% ($p<0.05$) in formulation UL003C-40 group, respectively.

Figure 10A:
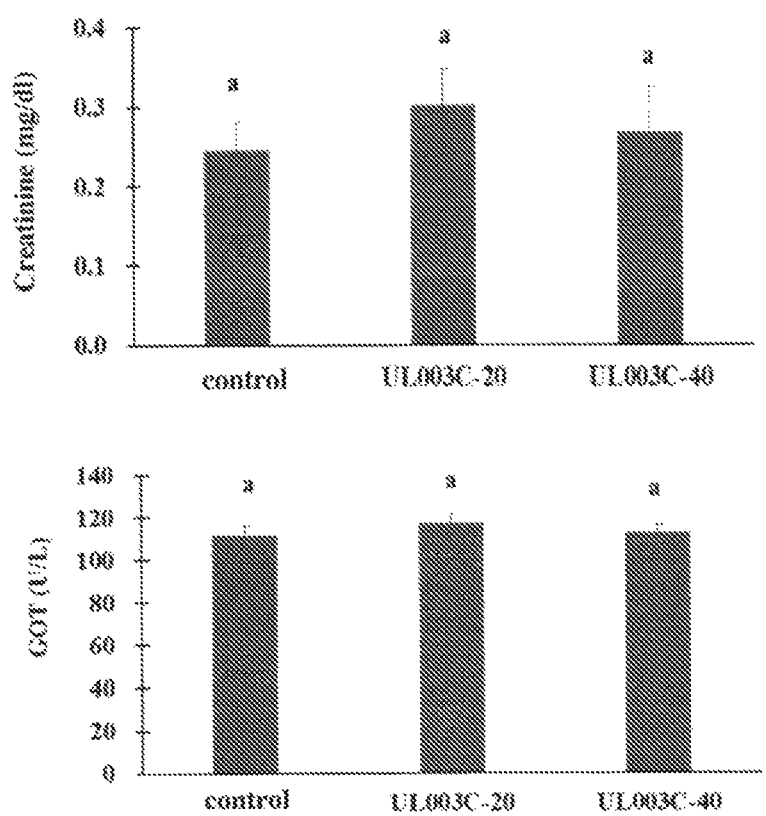
FIG. 10A illustrates the bar chart of serum biochemical index as creatinine and gluteamic oxaloacetic transaminase (GOT) in each group related to rats administered with high-fat diet (Control) to induce localized fat increasing and then localized injection.
Figure 10B:
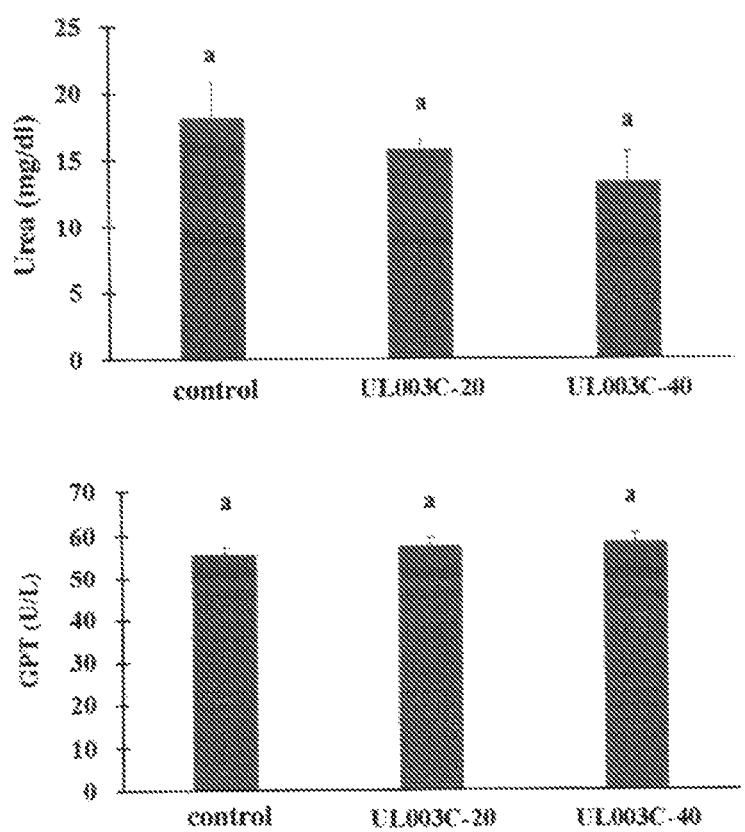
FIG. 10B illustrates the bar chart of serum biochemical index as urea and glutamic pyruvic transaminase (GTP) in each group related to rats administered with high-fat diet (Control) to induce localized fat increasing and then localized injection.

As shown in FIGS. 10A and 10B, no statistical difference ($p>0.05$) was found in serum biochemical marker of creatinine, urea, GOT, GPT indicated that formulation UL003C of the present invention at low- or high-dose would not cause side effects and be safe.

Example 9 Animal Assay (II)

Anti-apoptosis protein Bcl-2 and apoptosis-promoting protein Bax were key regulators in apoptotic pathway, the balance between these two proteins is important for the regulation of apoptosis. Higher Bcl-2 expression suppresses apoptosis while higher Bax expression promotes apoptosis. The ratio between these two protein determines the cell survival or apoptosis.

The protein expression of Bcl-2 and Bax2 in subcutaneous adipose tissue was determined with Western blot analysis and the ratio of Bax and Bcl-2 was evaluated as the apoptotic effect of formulation UL003C of the present invention.

Rats subcutaneous adipose tissues proteins from lower groin (injection site) of example 8 were extracted by 450 μl T-PER®. Thirty μg protein of each group was loaded and separated by polyacrylamide gel electrophoresis (SDS-PAGE) followed by transfer to PVDF membrane. Bcl-2 antibody (sc-7382) and Bax antibody (sc-526) were purchased from Santa Cruz. All data are presented as Mean±SD and different letters differ significantly among groups ($p<0.05$).

Figure 11:
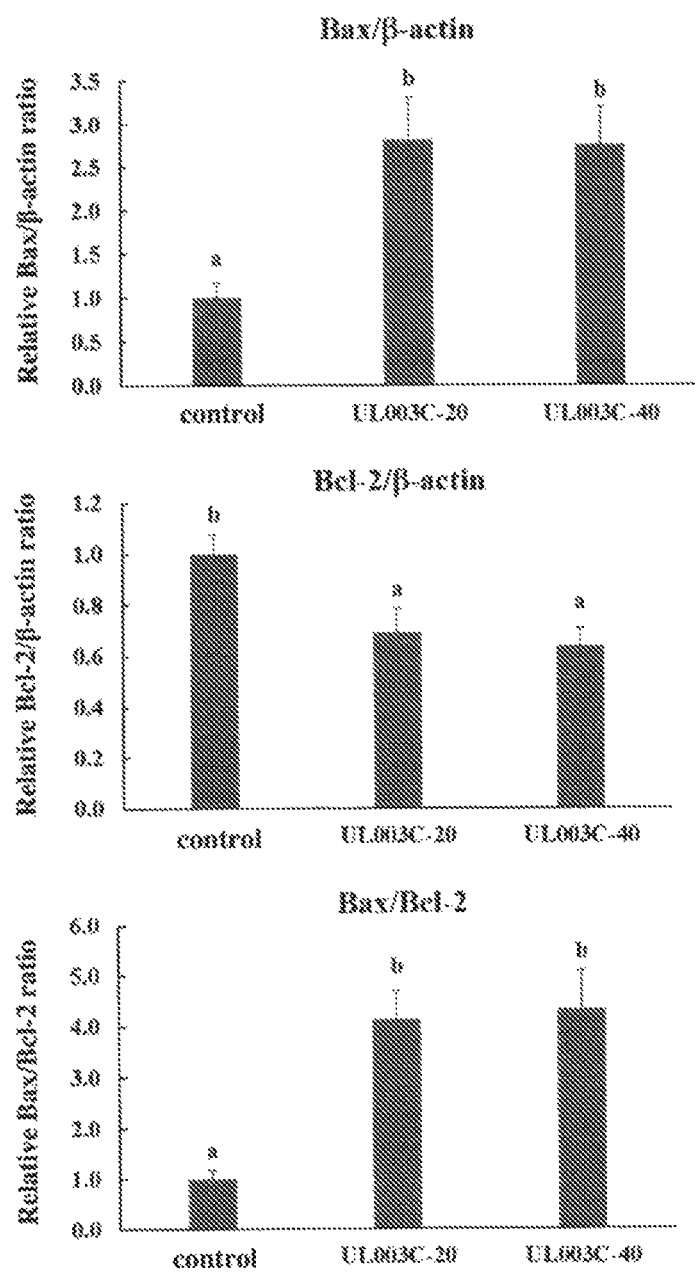
FIG. 11 illustrates the bar chart of apoptotic protein expression as Bax, Bcl-2, and ratio of Bax/Bcl-2 through Western Blotting in each group related to rats administered with high-fat diet (Control) to induce localized fat increasing and then localized injection.

As shown in FIG. 11, compared with that of control group, the formulation UL003C at low-dose and high-dose both enhanced the Bcl-2 expression ($p<0.05$) and inhibited Bax expression significantly ($p<0.05$), and the ratio of Bax/Bcl-2 was higher than that of control group ($p<0.05$). The results showed that formulation UL003C of the present invention was effective to promote apoptosis on adipocytes of injection adipose tissues.

The composition of the present invention was indeed effective to induce adipocyte apoptosis and reduce localized fat. The results of animal assays also confirmed the composition of the present invention can reduce adipocytes and localized fat via promoting apoptosis mechanism.

Even though numerous characteristics and advantages of the present invention are revealed and described as above, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for reducing localized fat at a local site of a subject, comprising a step of administering at the local site of the subject a therapeutically effective amount of a pharmaceutical composition comprising resveratrol and curcumin, wherein a weight ratio of resveratrol and curcumin ranges from 1:30 to 9:1.

2. The method as claimed in claim 1, wherein the subject is animal or human.

3. The method as claimed in claim 1, wherein the local site comprises face, jaw, arm, waist, abdomen or thighs.

4. The method as claimed in claim 1, wherein the step of administering comprises injection.

5. The method as claimed in claim 1, wherein the therapeutically effective amount of the pharmaceutical composition is from 0.4 mg/kg BW to 100 mg/kg BW.

6. The method as claimed in claim 5, wherein the therapeutically effective amount of the pharmaceutical composition is from 1 mg/kg BW to 60 mg/kg BW.

7. The method as claimed in claim 1, wherein said pharmaceutical composition has a weight ratio of resveratrol and curcumin in 1:19 to 9:1.

8. The method as claimed in claim 4, wherein the injection comprises subcutaneous fat injection, subcutaneous injection, or intravenous injection.

9. The method as claimed in claim 7, wherein the local site comprises face, jaw, arm, waist, abdomen or thighs.

10. The method as claimed in claim 7, wherein the step of administering comprises localized injection, subcutaneous implantation, implantable injection pump or transdermal administration.

11. The method as claimed in claim 10, wherein the localized injection comprises subcutaneous fat injection, or subcutaneous injection.

12. The method as claimed in claim 10, wherein the therapeutically effective amount of the pharmaceutical composition is from 0.4 mg/kg BW to 100 mg/kg BW.

13. The method as claimed in claim 12, wherein the therapeutically effective amount of the pharmaceutical composition is from 1 mg/kg BW to 60 mg/kg BW.

14. The method as claimed in claim 1, wherein the step of administering comprises subcutaneous implantation, implantable injection pump, or transdermal administration.

15. A method for weight loss of a subject, comprising a step of administering at a site of the subject a therapeutically effective amount of a pharmaceutical composition comprising resveratrol and curcumin, wherein a weight ratio of resveratrol and curcumin ranges from 1:30 to 9:1.

16. The method as claimed in claim 15, wherein the subject is animal or human.

17. The method as claimed in claim 15, wherein the step of administering comprises subcutaneous implantation, or implantable injection pump.

18. The method as claimed in claim 15, wherein the step of administering comprises localized injection.

19. The method as claimed in claim 15, wherein the therapeutically effective amount of the pharmaceutical composition is from 0.4 mg/kg BW to 100 mg/kg BW.

20. The method as claimed in claim 15, wherein the therapeutically effective amount of the pharmaceutical composition is from 1 mg/kg BW to 60 mg/kg BW.

21. The method as claimed in claim 15, wherein said pharmaceutical composition has a weight ratio of resveratrol and curcumin in 1:19 to 9:1.

22. The method as claimed in claim 18, wherein the localized injection comprises subcutaneous fat injection or subcutaneous injection.

23. The method as claimed in claim 21, wherein the step of administering comprises injection, subcutaneous implantation, or implantable injection pump.

24. The method as claimed in claim 23, wherein the injection comprises subcutaneous fat injection, subcutaneous injection or intravenous injection.

25. The method as claimed in claim 21, wherein the therapeutically effective amount of the pharmaceutical composition is from 0.4 mg/kg BW to 100 mg/kg BW.

26. The method as claimed in claim 21, wherein the therapeutically effective amount of the pharmaceutical composition is from 1 mg/kg BW to 60 mg/kg BW.

* * * * *